United States Patent

Bakos et al.

Patent Number: 5,026,895
Date of Patent: Jun. 25, 1991

[54] NOVEL (TRIFLUOROMETHYL)-PHENOXY-BENZOIC ACID DERIVATIVES, PROCESS FOR THE PREPARATION THEREOF AND FUNGICIDES CONTAINING THESE COMPOUNDS AS ACTIVE INGREDIENT

[75] Inventors: József Bakos; Bálint Neil, both of Veszprém; László Kollár, Szeged; Szilárd Torös, Pécs; Gvula Eifert, Dunaharaszti; Ferenc Bihari, Budapest; Péter Boros, Budapest; Anna Durkó née Pónácz, Budapest; István Küronya, Budapest; István Magyari, Stromfeld A.sétány; Judit Timár, Budapest; Péter Bohus, Budapest; László Wohl, Budapest, all of, Hungary

[73] Assignee: Budapesti Vegyimüvek, Budapest, Hungary

[21] Appl. No.: 797,373

[22] Filed: Nov. 12, 1985

[30] Foreign Application Priority Data

Nov. 12, 1984 [HU] Hungary ............................. 4191/84

[51] Int. Cl.$^5$ .................... C07C 205/00; A01N 37/12
[52] U.S. Cl. .................................. 560/21; 560/65; 562/435; 562/474
[58] Field of Search .................... 560/21, 85; 562/435, 562/474; 574/539, 544, 568

[56] References Cited

U.S. PATENT DOCUMENTS

| | | | |
|---|---|---|---|
| 3,957,852 | 5/1976 | Fujikawa et al. | 560/65 |
| 4,031,131 | 6/1977 | Johnson | 560/65 |
| 4,314,070 | 2/1982 | Schreiber et al. | 560/65 |
| 4,323,692 | 4/1982 | Tanger et al. | 560/65 |
| 4,384,135 | 5/1983 | Cartwright et al. | 560/65 |
| 4,388,472 | 6/1983 | Cartwright | 560/21 |
| 4,400,530 | 8/1983 | Grove | 560/21 |
| 4,424,393 | 1/1984 | Guzik | 560/21 |

Primary Examiner—Paul J. Killos
Attorney, Agent, or Firm—Schweitzer Cornman & Gross

[57] ABSTRACT

The invention relates to novel fungicidally active compounds, a process for the preparation thereof, composition comprising the said composition as active ingredient and their use for agricultural purpose.

The novel (trifluoromethyl)-phenoxy benzoic acid derivate can be described by formula (I),

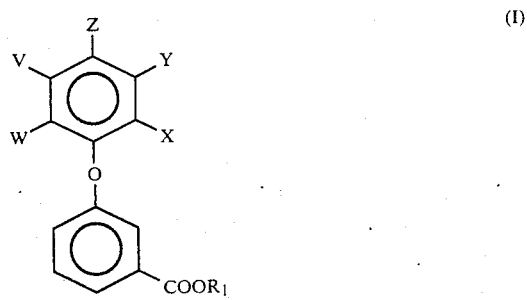

wherein
X is hydrogen or halogen, preferably chlorine, nitro or trifluoromethyl,
Y is hydrogen or halogen, preferably chlorine,
Z is hydrogen, trifluoromethyl or nitro,
V is hydrogen, halogen, preferably chlorine, or nitro,
W is hydrogen, nitro or trifluoromethyl,
$R_1$ is alkyl having 1-4 carbon atoms, preferably ethyl, hydrogen, alkali metal, preferably sodium, potassium, or ammonium or ammonium-ion having a formula (II),

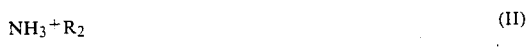

wherein
$R_2$ is alkyl having 1-4 carbon atoms, preferably isopropyl, hydroxyalkyl having 1-4 carbon atoms, preferably 2-hydroxyethyl, alkenyl having 2-4 carbon atoms, preferably propinyl, alkinyl having 2-4 carbon atoms, preferably propargyl, provided, that of X, Y, Z, V and W
a. at least one is different from hydrogen and/or chlorine, and
b. at most only two can be present having the same definition.

15 Claims, No Drawings

NOVEL (TRIFLUOROMETHYL)-PHENOXY-BENZOIC ACID DERIVATIVES, PROCESS FOR THE PREPARATION THEREOF AND FUNGICIDES CONTAINING THESE COMPOUNDS AS ACTIVE INGREDIENT

TECHNICAL FIELD

The invention relates to new fungicidally active compounds, a process for the preparation thereof, compositions comprising the said compounds as active ingredient and their use for agricultural purposes.

The invention provides the novel (trifluoromethyl)-phenoxy-benzoic acid derivatives of formula (I),

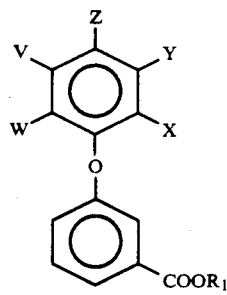

wherein
X is hydrogen or halogen, preferably chlorine, nitro or trifuoromethyl,
Y is hydrogen or halogen, preferably chlorine,
Z is hydrogen, trifluoromethyl or nitro,
V is hydrogen, halogen, preferably chlorine, or nitro,
W is hydrogen, nitro or trifluoromethyl
$R_1$ is alkyl having 1-4 carbon atoms, preferably ethyl, hydrogen, alkali metal, preferably sodium, potassium, or ammonium or ammonium-ion having a formula (II), $$NH_3^+R_2 \qquad (II)$$

wherein
$R_2$ is alkyl having 1-4 carbon atoms, preferably isopropyl, hydroxyalkyl having 1-4 carbon atoms, preferably 2-hydroxyethyl, alkenyl having 2-4 carbon atoms, preferably propinyl, alkinyl having 2-4 carbon atoms, preferably propargyl,
provided, that of X, Y, Z, V and W
a. at least one is different from hydrogen and/or chlorine, and
b. at most only two can be present having the same definition—as well as their salts or esters.

Further, the invention provides a process for the preparation of compounds of formula (I), fungicidal compositions comprising said compounds and a method for treating fungal infections of cultivated plants using said compounds or compositions.

BACKGROUND ART

The substituted phenoxy-benzene derivatives (formerly called diphenyl-ethers) have been known for twenty years as herbicides and have been used first of all in rice, cotton and soyabean plants. The derivatives substituted with trifluoromethyl were described 10 years later (e.g. E. Wegler: Chemie der Pflanzenschutz - und Schädligsbekämpfungsmittel Band 5., Springler-Verlag, Berlin, Heidelberg, N.Y., 1977, p. 73–80 and 401–407).

All the phenoxy-benzene derivatives described by Worthing Charles, R. (The Pesticide Manual, The Boots Company Ltd., Nottingham, England, 6. ed., 1979) are herbicides as well.

Kádár, A. has summarized in a manual all the commercial phenoxy-benzene derivatives but each of them are mentioned as herbicides. (Kádár, A.: "Chemical Weed control", Agricultural Publisher, Budapest, 1983, p. 74–76).

Most preferred phenoxy-benzene derivatives with an excellent herbicidal activity are e.g. the followings:
2-nitro-1-(4-nitrophenoxy)-4-(trifluoromethyl)-benzene (fluorodiphen, BP 1 033 163);
2-chloro-1-(4-nitrophenoxy)-4-(trifluoromethyl)-benzene
   (nitrofluorophen, DE-OS 2 304 006, BE 794 517);
2-chloro-1-(3-ethoxy-4-nitrophenoxy)-4-(trifluoromethyl)-benzene
   (oxyfluorophen, U.S. Pat. No. 3,798,276);
sodium 5-[2-chloro-4-(trifluoromethyl)phenoxy]-2-nitrobenzoate
   (acyfluorophen-sodium, U.S. Pat. No. 4,063,929);
ethyl-5-[2-chloro-4-(trifluoromethyl)phenoxy]-2-nitrobenzoate
   (acyfluorophen-ethyl, U.S. Pat. No. 3,928,416).

The closest phenoxy-2-nitrobenzoic acid derivatives to the present invention, but still having a different structure, are described as herbicides in the U.S. Pat. Nos. 3,928,416 and 4,063,929 (the latter corresponds to HUP No. 172 709).

SUMMARY OF THE INVENTION

Surprisingly, we found in the course of our experiments that the new, substituted (trifluoromethyl) phenoxy benzoic acid derivatives possess not only herbicidal but also an excellent fungicidal activity, furthermore they are not phytotoxic, so they are suitable for treating fungal infections of cultivated plants.

So the new compounds of the present invention enlarge not merely the variety of fungicides but also promote the control of fungi resistant to known fungicides, when they are used optionally in combination with other known fungicides.

DETAILED DESCRIPTION OF THE INVENTION

Therefore the present invention provides
a. new (trifluoromethyl)-phenoxy benzoic acid derivatives of formula (I), wherein
X is hydrogen or halogen, preferably chlorine, nitro or trifluoromethyl,
Y is hydrogen or halogen, preferably chlorine,
Z is hydrogen, trifluoromethyl or nitro,
V is hydrogen, halogen, preferably chlorine, or nitro
W is hydrogen, nitro or trifluoromethyl,
$R_1$ is alkyl having 1-4 carbon atoms, preferably ethyl, hydrogen, alkali metal, preferably sodium, potassium or ammonium or ammonium-ion having a formula (II), wherein
$R_2$ is alkyl having 1-4 carbon atoms, preferably isopropyl, hydroxyalkyl having 1-4 carbon atoms, preferably 2-hydroxyethyl, alkenyl having 2-4 carbon atoms, preferably prepinyl, alkinyl having 2-4 carbon atoms, preferably propargyl,
provided, that of X, Y, Z, V and W a. at least one is different from hydrogen and/or chlorine, and
b. at most only two can be present having the same definition—as well as their salts or esters.

b. fungicides comprising the new compounds of formula (I) or their salts or esters as active ingredient, wherein all substituents are the same as mentioned above, c. process for preparation the aforementioned new (trifluoromethyl)phenoxy benzoic acid derivatives of formula (I) and their salts and esters, d. method for treating fungal infections of cultivated plants using the aforementioned compounds of formula (I) or their salts or esters as active ingredient.

The novel (trifluoromethyl)phenoxy benzoic acid derivatives, according to the invention, can be prepared by any known method, e.g.

a. when using the known Ulmann's ether synthesis, the alkali metal salt of the appropriate phenol derivatives is reacted with the appropriate halogen-benzene derivative in the presence of a cuprous catalyst or without a catalyst. E.g. the sodium salt of 3-hydroxy benzoic acid or -benzoic acid-ester is reacted with the suitably substituted benzotrifluoride derivative or when using m-cresol the appropriate carboxylic acid derivative can be obtained hydrolysing the benzylidene trihalogen compound obtained with radical halogenation, but the reaction can also be carried out if the 3-halogen-benzoic acid or 3-halogen-benzoic acid-ester is reacted with the suitably substituted hydroxy benzotrifluoride derivative. Also the oxidation of m-cresol, 3-(aminomethyly)-, 3-(halogenmethyl)-(or 3-hydroxymethyl)-phenol yields also the appropriate carboxylic acid. In the course of the reaction carried out in any order, (trifluoromethyl)-phenyl-(or phenoxy) and 3-carboxy-phenoxy-(or phenyl) groups are coupled, thereafter the diphenylether thus obtained is substituted according to the definitions of X, Y, Z, V, W, $R_1$ and $R_2$ substituents, or a phenol-compound substituted according to the definitions of X, Y, Z, W, V and $R_1$ substituents is reacted with a halogen-benzene in the presence of a base;

b. the reaction can be carried out with a higher yield and within a shorter reaction time if dipolar-aprotic solvents (e.g. dimethyl formamide, dimethyl acetamide, sulfolane, dimethylsulfoxyde, acetone, etc.) are used. Choosing a solvent with the suitable boiling point the reaction can be carried out without a catalyst;

c. in the course of the ether-synthesis of type $S_N2$, a phenolate-anion and a neutral molecule (halogenbenzene) are reacted. When judging the function of the nucleophilic group to be coupled, the nucleophyl force and the sterical factors have to be considered. The quality of the group to be changed (usually halogen) and the activating effect of the different substituents being on the ring also have a very important effect on the reaction time.

According to a preferred method of the invention, compounds of formula (III)

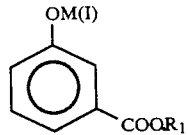

(III)

wherein $R_1$ is hydrogen, alkali metal or alkyl having 1-4 carbon atoms, and M(I) is hydrogen or alkali metal—is reacted with a substituted halogenbenzene of formula (IV)

(IV)

wherein X, Y, Z, V, and W are the same as mentioned above and Hal is halogen—in the presence of a solvent. As solvent preferably a dipolar-aprotic solvent or solvent-mixture can be used, e.g. dimethylformamide, dimethylacetamide, sulfolane, dimethylsulfoxide, etc. The reaction time is between several hours and one or two days, depending on the reaction temperature and on the position, number and quality of the halogen-substituents of the halogen-benzene compounds of formula (IV).

Preferably, the reaction is carried out in an inert atmosphere (e.g. in nitrogen or argon) and the reaction product can be recovered by well-known methods, e.g. by pouring the reaction mixture into water and separating the precipitated product, etc. The product can be purified, if desired, e.g. by recrystallization.

For preparation compounds of formula (I)—wherein $R_1$ is alkyl having 1-4 carbon atoms—preferably 3-hydroxy-benzoic acid alkylester of formula (III) is reacted with a halogenbenzene of formula (IV) in the presence of potassium carbonate, preferably dry potassium carbonate, then the precipitated potassium halogenide (e.g. potassium chloride) is filtered, the filtrate is evaporated, preferably in vacuo, and the product is isolated from the residue by dissolving or recrystallization.

The salts of the (trifluoromethyl) phenoxy benzoic acid derivatives of formula (I) can be obtained by any known method.

The invention provides fungicidal compositions comprising the compounds of formula (I) as active ingredient in an amount of 0.001–95% by weight in association with solid or liquid carrier(s), solvent(s) and optionally with other ingredient(s) (additive(s)). These compositions may, for example, be wettable powders (WP), emulsifiable concentrates (EC), suspension concentrates (SC), various types of water-miscible solution (SL), water-soluble concentrates (WSC), various granules (G), (WG), ULV compositions, foils, preferably seed-foils, etc.

The ingredients used in a composition according to the invention may for example be surface active agents, such as wetting agents, dispersing agents, emulsifying agents, anticakings, spreaders, antifoams, different agents which enhance the penetration and adhesion of the active ingredient, or enhance or maintain the biological activity thereof etc.

Suitable solid carriers and dilutents in a composition according to the invention include e.g. inert minerals, such as different kaolins, china clay, attapulgite, montmorrilonite, micaschist, piroffilite, bentonite, diatomaceous earth or synthetic silicas of high dispersity potassium carbonate, calcinated magnesia, dolomite, gypsum, tricalciumphosphate, Fuller's earthes, etc., further milled tobacco-stem or wood flour can also be used.

Suitable liquid carriers, diluents and solvents include e.g. water, organic and/or aqueous organic solvents, such as methanol, ethanol, n- and isoprpanol, diacetone-alcohol, benzylalcohol; glycoles, such as ethyleneglycol, diethylene-, triethylene- and propylene glycol; and the esters thereof, such as methylcellosolve, butyl diglycol; ketones, such as dimethylketone, methylethylketone, methylisobutylketone, n- or isopropylacetate, n- or isobutylacetate, amylacetate, isopropylmyristate, dioctylphtalate, dihexylphtalate, etc.; aromatic, aliphatic or alicyclic hydrocarbons, such as paraffine hydrocarbons, cyclohexane, cerosane, gasoline, benzene, toluene, xylene, tetraline, decaline; mixtures of alkylbenzenes; chlorinated hydrocarbons, such as trichloroethane, dichloromethane, perchloroethylene, dichloropropane, chlorobenzene, etc.; lactones, such as $\gamma$-butyrolactone, etc.; lactames, such as N-methylpyrrolidone, N-cyclohexylpyrrolidone; acidamides, such as dimethyl formamide etc.; different vegetable- and animal oils, such as sunflower-seed oil, linseed oil, olive oil, soybean oil, castor oil, sperm oil etc.

The suitable wetting-, dispersing, emulsifying, adhesion-enhancing agents, anticakings and spreaders may be of nonionic or ionic type.

As ionic agents the following compounds can be mentioned: the salts of saturated or unsaturated carboxylic acids; sulphonates of aliphatic, aromatic or aliphatic-aromatic-hyydrocarbons; sulphates of alkyl-, aryl- or aralkyl alcohols; sulphonates of the alkyl-, aryl- or aralkyl-esters and -ethers; sulphatated vegetable or animal oils; alkyl-, aryl- or aralkylphosphate esters; the various salts of the above-mentioned compounds formed with alkali- or alkali-earth metals or with organic bases, such as different amines or alkanolamines. For example: sodium-laurylsulphate, sodium-2-ethyl-hexylsulphate; sodium-, ethanolamine-, diethanol-amine-, triethanolamine or isopropylamine salt of dodecyl-benzenesulphonic acid; sodium salt of naphtalenesulphonic acid; sodium-diisooctylsulphosuccinate, sodium-xylenesulphonate; sodium- or calcium salt of petrole-sulphonic acid; soft soap; potassium-, sodium-, calcium-, aluminium- or magnesium-stearate, etc. The phosphate esters include e.g. phosphated alkylphenols—or esters of fatty-alcohols formed with polyglycols as well as their neutralized or partly neutralized forms with the above-mentioned cations or organic bases. Further, as anionic surface-active agent disodium-N-octadecyl-sulphosuccinate, sodium-N-oleyl 1-N-methyltrauzide, etc., as well as the different kinds of ligninesulphonates can be used.

Suitable nonionic wetting-, dispersing- and emulsifying agents include e.g. ethers of ethylene oxyde formed with alcohols having 10 to 20 carbon atoms, such as stearylpolyxyethylene, oleyilpolyoxyethylene; alkylphenol esters, such as the ester of stearinic acid or myristinic acid formed with polyethylene glycol or polyethyleneglycololeate, etc.; ethylene oxide and propylene oxide block-polymers; partial esters of fatty- and oleic acids formed with hexitolanhydrides, such as the ester of sorbitol formed with oleic acid or stearinic acid or condensation products of the above compounds formed with ethylene oxide; tertiary glycols, such as 3,6-dimethyl-4-octyn-2,6-diol or 4,7-dimethyl-5-decyn-4,7-diol; polyethyleneglycol-thioethers, such as the ether of dodecylmercaptane formed with polyethylene-glycol etc.

Suitable spreading agents include e.g. alkali-earth-metal soaps, salts of sulphosuccinic acid ester, natural and synthetic water-soluble polymers, such as casein, starch, vegetable gums, arabic gum, cellulose ethers, methylcellulose ethers, methylcellulose, hydroxyethylcellulose, polyvinylpyrrolidon, polyvinylalcohol, etc.

Suitable antifoam agents include e.g. polyoxyethylene and polyoxypropylene blockpolymers of low molecular weight; octyl-, nonyl-, phenylpolyoxyethylene/wherein the number of the ethylene-oxyde units are $>5/$; higher alcohols, such as octylalcohol etc; special silicon oils etc.

Using the suitable additives the different compositions can be made compatible from colloide-chemical points of view with any kind of fertilizer-system. The pesticidal compositions thus prepared may comprise other known pesticidal agents and/or nutrients as active ingredient besides the compounds of the invention.

In the preparation of wettable powders (WP) the active ingredient(s) as well as the other ingredient(s), surfactant(s) are admixed, ground and homogenized. When a liquid surfactant is employed it may also be e.g. sprayed onto the surface of the solid organic or inorganic carriers or to the powder mixture also comprising the solid active ingredient. Similar method is used in the case of liquid active ingredients. Alternatively the solid components ground previously may be suspended in organic solvents which contain the liquid surfactant, and this suspension may be e.g. spray-dried. So, the liquid surfactant is applied on to the surface of the solid active ingredient and diluent.

Emulsifiable concentrates (EC) can be prepared e.g. by dissolving the active ingredient(s) together with one of the above mentioned surfactants and emulsifying agents in a water miscible solvent. The emulsifiable concentrate thus obtained can form a spray emulsion upon admixing with water (spontaneously or by mechanical action) which is stable over a long period.

In the course of the preparation of a water-miscible solution concentrate (SL), the active ingredient and the suitable water soluble additives are dissolved in water and/or a water-miscible solvent. This composition can be diluted with water to obtain a spray having the desired concentration.

In the course of the preparation of water-soluble liquid concentrate (WSC) the active ingredient and the suitable water-soluble additives are dissolved in water or a water-miscible solvent. The composition thus obtained may be diluted to obtain a spray having the desired concentration.

The solution concentrate containing the active ingredient may also be dispersed in water-miscible solvent using a suitable emulsifying agent, in this case invert emulsion can be obtained. If always the most suitable solvents and surfactants are choosen, the compositions thus obtained form stable dispersions upon admixing with water or water-miscible liquids where the particles (even they are of molecular size) does not sedimentate from even over a long period.

In the preparation of suspension-concentrates (SC) the wetting and dispersing agents are dissolved optionally by heating in the mixture of water (preferably ionexchanged water). Then an anti-freeze component (preferably ethylene glycol or glycerol) and the solid active ingredient(s) being in powder or crystalline form) and optionally the anticaking component (e.g. Aerosil 200) are admixed under continuous stirring to this solution. Thereafter this grain-liquid system (i.e. slurry) is ground in a wet grinding-machine (e.g. in a closed Dyno-mill) to the desired particle size, which is generally at most 5 $\mu$m, in order to avoid sedimentation. After grinding the mixture is homogenized optionally with antifoam and thickening agents (e.g. Kelzan S). Optionally the order of the above steps may be changed or if desired, other components (e.g. pigments etc.) may be added.

The solid active ingredients may be combined with other liquid, water-immiscible or water-miscible active ingredients. The colloidal active ingredients having a low melting point can be used up in the form of a melt with or without an emulsifying agent.

The preparation of the compositions is similar to that of the EC or SC compositions.

Granules (G) for direct use can be obtained by extruding or by coating a milled carrier (e.g. milled limestone) or by adsorbing the liquid component(s) by an milled carrier having absorptive properties.

Granules suitable for spraying (WG) can be obtained from a WP and/or SC formulations by an agglomeration method e.g. granulation in a dragee pan using a thickening agent.

Diluting these compositions with water or inert diluent(s) sprays, dusting powders comprising less than 5% by weight, preferably 1 to 0.01% by weight of active ingredient can be obtained.

Such compositions can also be obtained by mixing the different sprays containing only one active ingredient just before use.

One of the preferred fungicidal composition according to the invention is the seed-foil. It is a well-known method in the horticulture as well as in the agriculture that in order to facilitate the sowing, to assure the uniform seed-and row-space, instead of hand-planting the seed-corns are incorporated into any kind of water-soluble foil and these foil-bands, that may contain the seed-corns in several raws are put into the soil. The foil may be made of any kind of an inert, water-soluble material, e.g. polyvinyl-alcohol the only demand in connection with it is, that it should not be harmful to the seeds and the moisture content of the soil could decompose or optionally dissolve it. The active ingredient can be incorporated into the said seed-foil or the seeds previously treated with the active ingredients according to the invention are incorporated into the foil.

The most common method for controlling and preventing the attack of prasitic fungi are as follows: treating of the seeds, spraying or dusting. The fungicides, e.g. the treating agents, sprays or dusting powders have to be applied to the locus of the infection or to the locus where the infection is derived from.

In order to protect the seed-corns from infections and to control fungi infecting the seed-corns in the soil, the seed-corns are treated. Particularly the mildew-like conidiumic fungi jeopardize the seed-corns and seedlings. E.g. Fusarium graminearum and Fusarium moniliforme causing the toxyc fusariosis of corn and Nigrospora oryzae causing the migrosporic dry-rot of maize are spread by seed-corns.

The treated seeds can be attacked by numerous other sorts of fungi e.g. members of genera Rhizoctonia, Penicillium or Helminthosporium, each of them are mildew-like conidiumic fungi. The infections caused by these fungi can be controlled by different known fungicides, e.g. by captan [1,2,5,6-tetrahydro-N-(trichloromethyl-thio)-phtalimide], applied in an amount of 0.5 to 0.6 kg calculated for 1 t of seeds.

The fungi damaging the foliage or/and crops (fruits) of the plants can be controlled by several kinds of treatment, e.g. by spraying or dusting. For instance, in case of apple the monilia is caused by *Spilocea pomi* (*Fusicladium dendriticum*) or in case of grape-vine greymould is caused by Botrytis cinerae. These sorts of fungi are also conidiumic type and can controlled by using a spray comprising captan in an amount of 120 g/100 liters of diluent.

The importance of conidiumic fungi is therefore emphasized as the compounds according to the invention are especially effective against them.

These fungi represent the Miniliales order of the Deuteromycetes class and the predominant part of them are vegetative multiplying forms of the ascomytes (Ascomytes class). Three different families cause especially great damage to cultivated plants.

Some genera of these families are summarized in the following table:

| genera | species |
| --- | --- |
| | a/ Moniliaceae family |
| Monilia | e.g. *M. Fructigena* |
| Aspergillus | e.g. *A. niger* |
| Penicillium | e.g. *P. crustaceum* |
| Botrytis | e.g. *B. cinerea* |
| Verticillium | e.g. *V. albo-atrum* |
| Cercosporella | e.g. *C. herpotrichoides* |
| | b/ Dematiaceae family |
| Thielaviopsis | e.g. *T. basicola* |
| Nigrospora | e.g. *N. oryzae* |
| Spilocea | e.g. *S. pomi* synonym *Fusicladium dendriticum* |
| Cladosproium | e.g. *C. fulvum* |
| Helminthosporium | e.g. *H. turcicum* |
| Cercospora | e.g. *C. beticola* |
| Alternaria | e.g. *A. solani* |
| Stemphylium | e.g. *S. radicinum* |
| | c/ Tuberculariaceae family |
| Fusarium | e.g. *F. graminearum* and different types of *F. oxysporum* |

As it has already been mentioned, all above fungi have a sexed form, too, for example *Spilocea pomi* is known as *Venturia inaequalis* or *Endostigma inaequalis*.

The above mentioned genera of mildew-like conidiumic fungi include many thousands of dangerous varieties but the speciality of the above mentioned species is that a fungicide which is effective against one type of them can control all of the listed fungi.

The efficiency of the compounds of the invention was tested on *Aspergillus niger, Botrytis cinerea* and 17 other conidiumic fungus species, but it is expected that the same data could have been obtained if any other fungus belonging to the order of Moniliales had been used. In the in vitro tests captan was used as control, the efficicacy is exporessed in ppm or mg/l. It is expected that the efficacy of the compounds of the invention related to that of captan would be similar in field tests, too.

The novel compounds of the invention, their preparation, formulation and biological activity are illustrated by the following, non-limiting examples.

The compounds of the invention were identified e.g. on the basis of their $^1$H-NMR spectra. The numbering of the protons corresponds to that of formula (V)

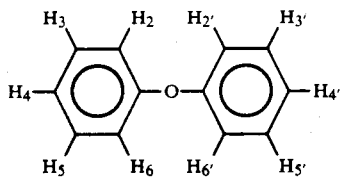

(V)

EXAMPLE 1

3-{[5-chloro-4-(trifluoromethyl)-2-nitro]-phenoxy}-benzoic acid (compound No. 1)

To the suspension of 10.7 g (0.05 mole) of 3-hydroxy-benzoic acid dipotassium salt and 2.5 g of potassium carbonate in 100 ml of acetone 13.0 g (0.05 mole) of 2,4-dichloro-5-nitro-benzotrifluoride in 50 ml of acetone were added dropwise and heated to reflux for 12 hours. Thereafter, the acetonic solution was poured into 200 ml of water, acified to pH 1 by adding concentrated hydrogen chloride, the acetone was sucked off, the precipitated light yellow solid was filtrated, washed with cold water and dried.

Yield: 14.5 g, (80.2%) in form of light yellow crystals.
Mp.: 175°-178° C.

$C_{14}H_7ClF_3NO_5$ Molecular weight: 361.5 (calculated).

MS: the ratio of 363 and 361 fragments of the molecule proves the compound substituted with one chlorine.

m/e (r.i.) = 363 (160) = $F_3C(Cl)(NO_2)C_6H_2OC_6H_4COOH$, 361 (480) = $F_3C(Cl)(NO_2)C_6H_2OC_6H_4COOH$, 344 (320) = $F_3C(Cl)(NO_2)C_6H_2OC_6H_4CO$, 316 (200) = $F_3C(Cl)(NO_2)C_6H_2OC_6H_4$, 224 (1000) = $F_3C(Cl)(NO_2)C_6H_2$.

IR spectrum: the OH vibrations of the carboxyl group appear in diffuse form and divided into partial peaks between 2400 and 3400 cm$^{-1}$. The $\nu$ C=O band appears at 1680 cm$^{-1}$, the $\nu$ as C—O—C band at 1330 cm$^{-1}$, the $\nu$ s C—O—C band at 1130 cm$^{-1}$. Salts of 3-{[5-chloro-4-(trifluoromethyl)-2-nitro]-phenoxy}-benzoic acid (compound No. 1) were obtained as follows:

5.6 g (0.0155 mole) of 3-{[5-chloro-4-(trifluoromethyl)-2-nitro]-phenoxy}-benzoic acid in 30 ml of diethylether were treated with 1.2 ml (0.91 g, 0.016 mole) of allylamine in 10 ml diethylether, thereafter the 2/3 part of the ether was sucked off and the product was precipitated with hexane.

Yield: 6.4 g (98%).
Mp.: 115°-123° C.

When producing ammonium salt, gaseous ammonia was conducted into the ehteric solution still gas evolution ceased, to produce sodium salt solid sodium hydroxyd was added in an equimolar amount, and to obtain the ethanol-ammonium-, isopropylammonium- and diethyl-2-propinylammonium salt the process as described by preparation of allylammonium salt was followed.

In the $^1$H NMR spectrum of the salts as listed above the aromatic protons appear at the same chemical displacement values:

$\delta_3 = 8.37$, $\delta_{4'} = 7.875$ (d, $J_{4'5'} = 8$ Hz), $\delta_{2'} = 7.127$, $\delta_{5'6'} = 7.25 - 7.55$, $\delta_6 = 7.1$ ppm.

Due to the salt formation, the characteristic band of the free carboxilic acid $\nu$ CO = 1680 cm$^{-1}$ disappears and $\nu$ as $CO_2^- = 1600-1620$ cm$^{-1}$ and $\nu$ s $CO_2^- = 1380$ cm$^{-1}$ appear as a broad band and a median sharp band, respectively.

The salts thus obtained and their physical constants are summarized in Table 1.

TABLE 1

| Compound No. | Name of the salts | Yield (%) | Melting point (°C.) |
|---|---|---|---|
| 1/a | Sodium-3-{[5-chloro-4-(trifluoromethyl)-2-nitro]-phenoxy}-benzoate | 74 | 262-265 |
| 1/b | ammonium-3-{[5-chloro-4-(trifluoromethyl)-2-nitro]-phenoxy}-benzoate | 79 | 175-183 |
| 1/c | isopropilammonium-3-{[5-chloro-4-(trifluoromethyl)-2-nitro]-phenoxy}-benzoate | 78 | 101-109 |
| 1/d | allilammonium-3-{[5-chloro-4-(trifluoromethyl)-2-nitro]-phenoxy}-benzoate | 98 | 115-123 |
| 1/e | ethanolammonium-3-{[5-chloro-4-(trifluoromethyl)-2-nitro]-phenoxy}-benzoate | 85 | 90 |
| 1/f | diethyl-2-propinylammonium-3-{[5-chloro-4-(trifluoromethyl)-2-nitro]-phenoxy}-benzoate | 95 | oil |

EXAMPLE 2

3-[2-(trifluoromethyl)-phenoxy]-benzoic acid (compound No. 2)

10.7 g of (0.05 mole) 3-hydroxy-benzoic acid dipotassium salt, 2.5 g of dry potassium carbonate and 9.0 g (0.05 mole) of 2-chloro-benztrifluoride were suspended in 50 ml of dimethylsulphoxyde and heated at 140°-144° C. for 16 hours, under stirring. Thereafter, the dimethylsulphoxide was sucked off, the residue dissolved in 200 ml of water and the solution acified by concentrated hydrogen chloride to pH 1. The product was filtered, washed with cold water and dried.

Yield: 2.3 g (16.3%) in form of white crystals.
M.p.: 144°-147° C.

$C_{14}H_9F_3O_3$ Molecular weight: 282 (calculated).

MS: characteristic fragments are the following:
m/e (r.i.) = 282 (1000) = $F_3CC_6H_4OC_6H_4COOH$, 265 (120) = $F_3CC_6H_4OC_6H_4COOH$, 237 (230) = $F_3CC_6H_4OC_6H_4$, 236 (140) = $F_3CC_6H_4OC_6H_3$, 217 (100) = $F_2CC_6H_4OC_6H_3$.

IR spectrum: $\nu$ OH(COOH) = 2400-3400 cm$^{-1}$; $\nu$ C=O = 1680 cm$^{-1}$; $\nu$ as C—O—C = 1330 cm$^{-1}$; $\nu$ s C—O—C = 1130 cm$^{-1}$.

The salts of the above compound were obtained according to the processes described in Example 1.

EXAMPLE 3

3-{[2-chloro-4-(trifluoromethyl)-6-nitro]-phenoxy}-benzoic acid (compound No. 3)

Following the procedure of Example 2 but using 3,4-dichloro-5-nitrobenztrifluoride for 2-chloro-benztrifluoride and heating the reaction mixture at 110°-120° C. for 6 hours the title product was obtained.

Yield: 12.5 g, (67%) in form of brown crystals.

M.p.: 115°–120° C.
C$_{14}$H$_7$O$_5$NClF$_3$; Molecular wight: 361 (calculated).
MS: characteristic fragments are as follows:

m/e (r.i.)=361 (1000)=F$_3$C(Cl)(NO$_2$)C$_6$H$_2$OC$_6$H$_4$COOH, 344 (70)=F$_3$C(Cl)(NO$_2$)C$_6$H$_2$OC$_6$H$_4$CO, 279 (280)=F$_2$O(Cl)C$_6$H$_2$OC$_6$H$_4$, 121 (130)=C$_6$H$_4$COOH.

IR spectrum: $\nu$ OH(COOH)=2400–3400 cm$^{-1}$; $\nu$ C=O=1700 cm$^{-1}$.

The salts of this compound were obtained according to the processes described in Example 1.

EXAMPLE 4

3-{[2-chloro-4-(trifluoromethyl)-5-nitro]-phenoxy}-benzoic acid (compound No. 4)

Following the procedure of Example 1 but using 3,4-dichloro-6-nitro-benzotrifluoride for 2,4-dichloro-5-nitro-benzotrifluoride and heating the mixture at its boiling pont for 8 hours the title product was obtained. Yield: 15.2 g (84%) in form of tan crystals.

M.p.: 178°–186° C.
Molecular weight: 361 (calculated).
MS: characteristic fragments are as follows:

m/e (r.i.)=361 (510)=F$_3$C(Cl)(NO$_2$)C$_6$H$_2$OC$_6$H$_4$COOH, 344 (190)=F$_3$C(Cl)(NO$_2$)C$_6$H$_2$OC$_6$H$_4$CO, 316 (130)=F$_3$C(Cl)(NO$_2$)C$_6$H$_2$OC$_6$H$_4$, 137 (1000)=OC$_6$H$_4$COOH.

The different salts of this compound were obtained according to the processes described in Example 1.

EXAMPLE 5

3-[3-chloro-4-(trifluoromethyl)-phenoxy]-benzoic acid (compound No. 5)

Following the procedure of Example 2 but using 2,4-dichloro-benzodifluoride for 2-chloro-benztrifluoride the title product was obtained.

Yield: 8.0 g (51%) in form of white crystals.
M.p.: 90°–91° C.
C$_{14}$H$_8$ClF$_3$O$_3$ Molecular weight: 316.6 (calculated).
MS: characteristic fragments are as follows:

m/e (r.i.)=316 (1000)=F$_3$C(Cl)C$_6$H$_3$OC$_6$H$_4$COOH, 297 (80)=F$_2$C(Cl)C$_6$H$_3$OC$_6$H$_4$COOH, 271 (150)=F$_3$C(Cl)C$_6$H$_3$OC$_6$H$_4$, 236 (210)=F$_3$CC$_6$H$_3$OC$_6$H$_4$.

IR spectrum: $\nu$ OH(COOH)=2400–3300 cm$^{-1}$, $\nu$ C=O=1680 cm$^{-1}$.

The salts of this compound were obtained following the procedure of Example 1.

EXAMPLE 6

3-{[3-chloro-4-(trifluoromethyl)-2,6-dinitro]-phenoxy}-benzoic acid-ethyl ester (compound No. 6)

To a two-necked round-bottom flask 5 g (0.03 mole) of 3-hydroxy-benzoic acid ethylester and 4.15 g (0.03 mole) of dry potassium carbonate were charged in nitrogen atmosphere and suspended in 30 ml of acetone, then under a slow stirring for 5 hours, 18.3 g (0.06 mole) of 2,4-dichloro-3,5-dinitro-benztrifluoride in 20 ml of acetone was added. The stirring was continued for 20 hours at room-temperature, the precipitated potassium chloride filtrated, the filtrate was evaporated and the residue recrystallized from 60 ml of methanol.

Yield 5.6 g (43.0%) in form of yellowish white powder.
C$_{16}$H$_{10}$O$_7$N$_2$ClF$_3$; M.p.: 86°–87° C.
Molecular weight: 434.5 (calculated).

The MS proves the compound substituted with one chlorine, and the isotopes having 35 and 37 mass number result in double peaks at m/e values of 434(436), 389(391).

m/e (r.i.)=434/436(740/280)=F$_3$CCl(NO$_2$)$_2$C$_6$HOC$_6$COOC$_2$H$_5$, 389/391(950/330)=F$_3$CCl(NO$_2$)$_2$C$_6$HOC$_6$H$_4$CO, 165 (800)=OC$_6$H$_4$COOC$_2$H$_5$, 137 (520)=OC$_6$H$_4$COOH, 121 (1000)=C$_6$H$_5$COO, 93 (300)=C$_6$H$_5$.

The $^1$H NMR proves also the above structure: $\delta_5$=8.46, $\delta_{4'}$=7.8 (J$_{4'5'}$=7 Hz, J$_{4'2'}$=1.5 Hz), $\delta_{6'}$=7.06 (J$_{6'5'}$=8 Hz, J$_{6'2'}$=2 Hz), $\delta_{CH2}$=3.275 (q, J=7 Hz), $\delta_{CH3}$=1.3 ppm t, J=7 Hz).

The IR spectrum proves more than one NO$_2$ groups. The symmetrical and asymmetrical valency vibration bands of the C—O—C bond are especially intensive at 1150 and 1300 cm$^{-1}$.

EXAMPLE 7

3-{[2-chloro-4-(trifluoromethyl)-5-nitro-]-phenoxy}-benzoic acid ethyl ester (compound No. 7)

Following the procedure of Example 6 but using 3,4-dichloro-6-nitro-benzotrifluoride for 2,4-dichloro-3,5-dinitro-benzotrifluoride and the product thus obtained was dissolved in 50 ml of acetone, the solution was cooled and some methanol was poured onto its surface, and after stirring the precipitated solid was filtrated and washed with methanol.

Yield: 6.0 g (61.3%) in form of yellovisch-white powder.
M.p.: 64°–65° C.

The MS proves that the test-compound contains one chlorine, as the two biggest fragments give a double-sign according to the ratio of the $^{35}$Cl and $^{37}$Cl isotopes.

m/e (r.i.)=389/391(750/260)=F$_3$CCl(NO$_2$)C$_6$H$_2$OC$_6$H$_4$COOC$_2$H$_5$, 344/346(870/280)=F$_3$CCl(NO$_2$)C$_2$H$_2$OC$_6$H$_4$CO, 165 (550)=OC$_6$H$_4$COOC$_2$H$_5$, 121 (1000)=C$_6$H$_5$COO.

The $^1$H NMR spectrum also proves the above structure: $\delta_6$=8.07 (d, J$_{63}$=1 Hz), $\delta_3$=8.9 (d, J$_{36}$=1 Hz), $\delta_{4'}$=7.7 (J$_{4'5'}$=8 Hz), $\delta_{6'}$=6.95 (J$_{6'5'}$=7 Hz), $\delta_{CH2}$=4.25 (q, J=7 Hz), $\delta_{CH3}$=1.3 ppm (t, J=7 Hz).

EXAMPLE 8

3-{[4-(trifluoromethyl)-2,6-dinitro]-phenoxy}-benzoic acid ethyl ester (compound No. 8)

To a two-necked flack 5.0 g (0.03 mole) of 3-hydroxy-benzoic acid ethyl ester, 6.77 g (0.03 mole) of 4-chloro-2,6-dinitro-benzotrifluoride and 4.15 g (0.03 mole) of dry potassium carbonate were charged and suspended in 50 ml of dry acetone in inert atmosphere, stirred for 40 hours, the precipitated solid potassium chloride was filtered and the redish solution evaporated in vacuo. Thereafter, the acetone was sucked off and the tan product was heated in 35 ml of isopropyl alcohol. The precipitated loose solid (4.8 g) was filtrated, the filtrate evaporated, the residue recrystallized from 25 ml of methanol, thus a further product in an amount of 3.5 g was obtained.

Yield: 8.3 g (69%) in form of light yellow, loose solid.
M.p.: 59°–60° C.;
C$_{16}$H$_{11}$O$_7$N$_2$F$_3$ Molecular weight: 400 (calculated).
MS: characteristic fragments are the followings:

m/e (r.i.)=400 (810)=F$_3$C(NO$_2$)$_2$C$_6$H$_2$OC$_6$H$_4$COOC$_2$H$_5$ 355 (1000)=F$_3$C(NO$_2$)$_2$C$_6$H$_2$OC$_6$H$_4$CO 165 (520)=OC$_6$H$_4$COOC$_2$H$_5$ 137 (320)=OC$_6$H$_4$COO, 121 (660)=C$_6$H$_3$NO$_2$.

$^1$H NMR: $\delta_{3(5)}=8.4$, $\delta_{CH_2}=4.25$ (q, J=7 Hz), $\delta_{CH_3}=1.27$ ppm (6, J=7 Hz).

IR spectrum: $\nu$ C=O=1725, $\nu$ as NO$_2$=1560, $\nu$ as C—O—C=1290, $\nu$ s C—O—C=1155 cm$^{-1}$.

EXAMPLE 9

3-{[2-(trifluoromethyl)-4-nitro]-phenoxy}-benzoic acid ethyl ester (compound No. 9)

To a two-necked round bottom flask 10.0 g (0.06 mole) of 3-hydroxy-benzoic acid ethyl ester, 13.53 g (0.06 mole) of 2-chloro-5-nitro-benztrifluoride and 8.3 g (0.06 mole) of potassium carbonate were charged and suspended in 100 ml of acetone and heated to reflux for 8 hours, the precipitated potassium salt was filtered, the filtrate evaporated, and the residue recrystallized from methanol.

Yield: 15.0 g 70.4% in form of sand-coloured solid.
M.p.: 63° C.
C$_{16}$H$_{12}$O$_5$NF$_3$; Molecular weight: 355 (calculated).
MS: characteristic fragments are the followings:
m/e (r.i.)=355 (680)=F$_3$C(NO$_2$)C$_6$H$_3$OC$_6$H$_4$COOC$_2$H$_5$, 341 (280)=F$_3$C(NO$_2$)C$_6$H$_3$OC$_6$H$_4$COOCH$_3$, 327 (300)=F$_3$C(NO$_2$)C$_6$H$_3$OC$_6$H$_4$COOH, 310 (1000)=F$_3$C(NO$_2$)C$_6$H$_3$OC$_6$H$_4$CO.

The $^1$H NMR also proves the above structure $\delta_3=8.5$ (d, $J_{35}=2$ Hz), $\delta_5=8.22$ (dd, $J_{53}=2$ Hz, $J_{56}=8$ Hz), $\delta_6=7.25$, $\delta_{4'}=7.92$ (d, $J_{4'5'}=8$ Hz), $\delta_{2'}=7.7$; $\delta_{5'}=7.5$ (dd, $J_{5'4'}=J_{5'6'}=8$ Hz), $\delta_{6'}=6.85$ (d, $J_{6'5'}=8$ Hz), $\delta_{CH_2}=4.325$ (q, J=7 Hz), $\delta_{CH_3}=1.325$ ppm (t, J=7 Hz).

EXAMPLE 10

3-{[2-chloro-4-(trifluoromethyl)-6-nitro]-phenoxy}-benzoic acid ethyl ester (compound No. 10)

Following the procedure of Example 6 but using 3,4-dichloro-5-nitro-benzotrifluoride for 2,4-dichloro-3,5-dinitro-benzotrifluoride the title product was obtained.

Yield: 7.4 g (63.3%) in form of yellowish-white solid.
M.p.: 79°-80° C.
C$_{16}$H$_{11}$O$_5$NClF$_3$ Molecular weight: 389.5 (calculated).
MS: characteristic fragments are the followings:
m/e (r.i.)=389/391 (1000/330)=F$_3$C(Cl)(NO$_2$)C$_6$H$_2$OC$_6$H$_3$COOC$_2$H$_5$, 361/363 (590/210)=F$_3$C(Cl)(NO$_2$)C$_6$H$_2$OC$_6$H$_3$COOH, 344/346 (980/320)=F$_3$C(Cl)(NO$_2$)C$_6$H$_2$OC$_6$H$_3$CO, 298/300 (420/140)=F$_3$C(Cl)C$_6$H$_2$OC$_6$H$_3$CO.

EXAMPLE 11

3-{[2-nitro-4-(trifluoromethyl)-5-chloro]-phenoxy}-benzoic acid ethyl ester (compound No. 11).

Following the procedure of Example 7 but using 3-nitro-4,6-dichloro-benzotrifluoride for 3,4-dichloro-benzofluoride the title product was obtained.

Yield: 16.4 g (70%) in form of white crystals.
M.p.: 95°-97° C.
C$_{16}$H$_{11}$O$_5$NClF$_3$ Molecular weight: 389.5 (calculated).
MS: characteristic fragments are the followings:
m/e (r.i.)=391 (220)=F$_3$C(Cl)(NO$_2$)C$_6$H$_2$OC$_6$H$_4$COOC$_2$H$_5$, 389 (580)=F$_3$C(Cl)(NO$_2$)C$_6$H$_2$OC$_6$H$_4$COOC$_2$H$_5$, 344 (870)=F$_3$C(Cl)(NO$_2$)C$_6$H$_2$OC$_6$H$_4$CO, 270 (210)=F$_3$C(Cl)C$_6$H$_2$OC$_6$H$_4$, 224 (420)=F$_3$C(NO$_2$)(Cl)C$_6$H$_2$.

IR spectrum: $\nu$ C=O=1720 cm$^{-1}$.

EXAMPLE 12

3-{[6-(trifluoromethyl)-2,4-dinitro]-phenoxy}-benzoic acid ethyl ester (compound No. 12)

Following the procedure of Example 6 but using 2-chloro-3,5-dinitro-benzotrifluoride for 2,4-dicloro-3,5-dinitro-benzotrifluoride the title product was obtained.

Yield: 11.5 g (95.8%) in form of light yellow solid.
M.p.: 87° C.
C$_{16}$H$_{11}$O$_7$N$_2$F$_3$ Molecular weight: 400 (calculated).
MS: the characteristic fragments are the followings:
m/e (r.i.)=400 (1000)=F$_3$C(NO$_2$)$_2$C$_6$H$_2$OC$_6$H$_4$COOC$_2$H$_5$, 355 (960)=F$_3$C(NO$_2$)$_2$C$_6$H$_2$OC$_6$H$_4$CO, 165 (560)=OC$_6$H$_4$COOC$_2$H$_5$, 121 (510)=C$_6$H$_3$NO$_2$.

Formulation Examples

EXAMPLE 13

Suspension concentrate (SC)

| | |
|---|---|
| Active ingredient (compound No. 2) | 50% by weight |
| Ethylene glycol | 8.0% by weight |
| Nonylphenol polyglycol ether (10 EO) | 5.0% by weight |
| Polysaccharide | 0.1% by weight |
| Silicone oil | 1.5% by weight |
| Water | 35.4% by weight |

EXAMPLE 14

Wettable powder (WP)

| | |
|---|---|
| Active ingredient (compound No. 7) | 90.0% by weight |
| Silica of high dispersity | 5.0% by weight |
| Disperging agent | 5.0% by weight |

EXAMPLE 15

Granule (G)

| | |
|---|---|
| Active ingredient (compound No. 8) | 5.0% by weight |
| Limestone (grounded) | 69.0% by weight |
| Ethylene glycol | 3.0% by weight |
| Silica of high dispersity | 5.0% by weight |
| Sodium ligninsulphonate | 3.0% by weight |
| Water | 13.5% by weight |

EXAMPLE 16

Dry flowable granule (WG)

| | |
|---|---|
| Active ingredient (compound No. 9) | 80.0% by weight |
| Sodium laurylsulphate | 2.0% by weight |
| Sodium ligninsulphate | 7.0% by weight |
| Water | 9.0% by weight |
| Kaolin | 8.0% by weight |

EXAMPLE 17

Water-soluble liquid concentrate (WSC)

| | |
|---|---|
| Active ingredient (compound No. 1/a) | 30.0% by weight |
| Ethylene glycol | 5.0% by weight |
| Nonylphenyl polyglycol ether (EO = 10, e.g. Arcopal N-100) | 2.0% by weight |
| Water ionexchanged | 67.0% by weight |

EXAMPLE 18

Emulsifiable concentrate (EC)

| | |
|---|---|
| Active ingredient (compound No. 8) | 40.0% by weight |
| Xylene | 12.0% by weight |
| Cyclohexanone | 20.0% by weight |
| Isophorone | 20.0% by weight |
| Polyoxyethylene-sorbitane monooleate | 5.0% by weight |
| Nonylphenyl-polyglycolether | 3.0% by weight |

EXAMPLE 19

Emulsifiable concentrate (EC)

| | |
|---|---|
| Active ingredient | 20.0% by weight |
| Xylene | 60.0% by weight |
| Isophorone | 8.0% by weight |
| Polyoxyethylene-sorbitane monooleate | 5.0% by weight |
| Tributylphenyl-polyglycol ether | 7.0% by weight |

EXAMPLE 20

Seed-foil a. To 615 g of water having a temperature of 60° C. 80 g of polyvinylalcohol (of the type RHODOVIOL 4/125 P, the viscosity of an aqueous solution thereof is 4 cP at 20° C., hydrolisation degree 89 mole %) were charged under stirring. After dissolution 20 g of polyvinylalcohol (of the type RHODOVIOL 30/20 m, the viscosity of a 4% aqueous solution thereof is 30 cP at 20° C., hydrolysation degree 98 mole %) and 20 g of glycerol were added and vigorously stirred until a homogenous solution was obtained. Thereafter the solution was allowed to stand while the bubbles could escape. The solution thus obtained was poured onto a glass sheet in a thickness of 0.5 mm using a ductur knife and dried at room temperature. The foil thus obtained comes off from the glass sheet, its thickness is 0.05–0.06 mm, it is easy to handle and has absorptive properties (control foil).

b. The procedure described above was followed but a solution containing 0.12 g of active ingredient (compound No. 6) suspended in 5 ml of water was used for the foil casting. After bubble release and casting, a foil having similar properties as the control foil but containing 1000 ppm of active ingredient was obtained.

c. Following the procedure of item b. but using a solution containing 0.012 g active ingredient (compound No. 3) suspended in 5 ml of water for the casting, a foil containing 100 ppm active ingredient was obtained.

d. Following the above procedure a foil comprising any compound according to the invention can be obtained.

EXAMPLE 21

Fungicidal activity

In order to determine the fungicidal activity of the compounds according to the invention the "poisioned" agar-sheet-method was used. To the compositions containing the compounds to be tested water and potato-agar culture medium containing 2% of dextrose were added in an amount which was sufficient to reach the desired concentration of the active ingredient to be tested.

The culture medium containing the compound to be tested in the desired concentration was poured into Petri dishes, allowed to solidify and inoculated with mycellium-disc of the same size cut out from pure fungus cultures. Thereafter the Petri-dishes were incubated for 3–7 days under conditions meeting the demands of the fungi to be tested.

The evaluation was carried out by measuring the diameter of the mycelliums and the ratio of the diameter of the treated and untreated cultures was calculated. If the diameter of the treated culture was the same as that of the untreated control, the protection was considered to be 0%.

The test result obtained by different active ingredient concentrations are summarized in Tables 2 and 3. As test fungi, Fusarium graminearum, Stemphylium radicium and Aspergillus niger, while as control compound captan were employed.

The data of the tables show that the compounds according to the invention possess similarly good or better activity than the known captan.

TABLE 2

| Active ingredient (ppm) | Activity in protection % | | | | | | | | | Captan (control) |
|---|---|---|---|---|---|---|---|---|---|---|
| | No. of the active ingredient | | | | | | | | | |
| | 1 | 2 | 3 | 4 | 6 | 7 | 8 | 9 | 10 | |
| *Fusarium graminearum* | | | | | | | | | | |
| 500 | 100 | 100 | 82 | 52 | 100 | 80 | 99 | 100 | 60 | 90 |
| 100 | 83 | 100 | 69 | 34 | 99 | 73 | 81 | 99 | 41 | 71 |
| 20 | 74 | 96 | 61 | 12 | 99 | 66 | 74 | 99 | 33 | 30 |
| 4 | 72 | 86 | 54 | 0 | 81 | 66 | 69 | 81 | 28 | 8 |
| *Stemphylium radicinum* | | | | | | | | | | |
| 500 | 100 | 92 | 79 | 26 | 88 | 75 | 84 | 84 | 59 | 84 |
| 100 | 84 | 80 | 63 | 22 | 72 | 69 | 72 | 66 | 48 | 72 |
| 20 | 57 | 80 | 58 | 22 | 63 | 66 | 69 | 63 | 33 | 54 |
| 4 | 54 | 71 | 52 | 10 | 60 | 54 | 66 | 63 | 22 | 35 |
| *Aspergillus niger* | | | | | | | | | | |
| 500 | 96 | 91 | 80 | 33 | 86 | 83 | 89 | 89 | 71 | 86 |
| 100 | 87 | 82 | 61 | 10 | 81 | 82 | 83 | 79 | 52 | 70 |
| 20 | 78 | 68 | 34 | 0 | 75 | 79 | 83 | 79 | 23 | 30 |
| 4 | 71 | 65 | 31 | 0 | 75 | 77 | 79 | 70 | 18 | 7 |

TABLE 3

| Active ingredient (ppm) | Activity in protection % | | | | | | | | Captan (control) |
|---|---|---|---|---|---|---|---|---|---|
| | No. of the active ingredient | | | | | | | | |
| | 1 | 1/a | 1/b | 1/c | 1/d | 1/e | 1/f | 5/a | |
| *Fusarium graminearum* | | | | | | | | | |
| 500 | 100 | 92 | 77 | 94 | 92 | 85 | 100 | 90 | 90 |
| 100 | 83 | 77 | 77 | 82 | 85 | 72 | 86 | 82 | 71 |
| 20 | 74 | 72 | 62 | 68 | 72 | 68 | 68 | 44 | 30 |
| 4 | 72 | 67 | 60 | 67 | 68 | 62 | 50 | 32 | 8 |
| *Stemphylium radicinum* | | | | | | | | | |
| 500 | 100 | 100 | 82 | 79 | 79 | 79 | 88 | 82 | 84 |

TABLE 3-continued

| Active ingredient (ppm) | Activity in protection % |  |  |  |  |  |  |  | Captan (control) |
|---|---|---|---|---|---|---|---|---|---|
| | No. of the active ingredient | | | | | | | | |
| | 1 | 1/a | 1/b | 1/c | 1/d | 1/e | 1/f | 5/a | |
| 100 | 84 | 82 | 82 | 49 | 58 | 52 | 78 | 70 | 72 |
| 20 | 57 | 55 | 52 | 40 | 42 | 21 | 41 | 51 | 54 |
| 4 | 54 | 42 | 37 | 40 | 42 | 27 | 24 | 32 | 35 |
| *Aspergillus niger* | | | | | | | | | |
| 500 | 96 | 94 | 90 | 89 | 89 | 89 | 90 | 88 | 86 |
| 100 | 87 | 86 | 76 | 80 | 86 | 82 | 60 | 72 | 70 |
| 20 | 78 | 76 | 63 | 58 | 61 | 61 | 37 | 33 | 30 |
| 4 | 71 | 72 | 63 | 51 | 62 | 46 | 27 | 21 | 7 |

What we claim is:

1. A fungicidal composition comprising as active ingredient an amount of from about 0.001 to about 95% by weight of a following acid or its salt:
3-{[5-chloro-4-(trifluoromethyl)-2-nitro]-phenoxy}-benzoic acid;
3-[2-(trifluoromethyl)-phenoxy]-benzoic acid;
3-{[2-chloro-4-(trifluoromethyl)-6-nitro]-phenoxy}-benzoic acid;
3-{[2-chloro-4-(trifluoromethyl)-5-nitro]-phenoxy}-benzoic acid; or
3-[3-chloro-4-(trifluoromethyl)phenoxy]-benzoic acid; or mixtures thereof.

2. A fungicidal composition of claim 1, wherein the salt is a sodium-, potassium-, ammonium-, isopropyl-, isopropyl-ammonium-, allyl-ammonium-, ethanol-ammonium-, or diethyl-2-propinyl-ammonium- salt of the acid.

3. A fungicidal composition comprising as active ingredient an amount of from about 0.001 to about 95% by weight of a following ethyl ester of the compound:
3-{[3-chloro-4-(trifluoromethyl)-2,6-dinitro]-phenoxy}-benzoic acid;
3-{[2-chloro-4-(trifluoromethyl)-5-nitro]-phenoxy}-benzoic acid;
3-[4-(trifluoromethyl)-2-6-dinitro]-benzoic acid;
3-{[2-(trifluoromethyl)-4-nitro]-phenoxy}-benzoic acid; or
3-{[2-chloro-4-(trifluoromethyl)-6-nitro]-phenoxy}-benzoic acid;
or mixtures thereof.

4. A method of treating fungal infections of cultivated plants, which comprises treating the soil, the seeds of the plant, the plant, or a part of the plant with a fungicidally effective amount of a novel, substituted trifluoromethyl-phenoxy-benzoic acid, or its salt or ester, having the formula

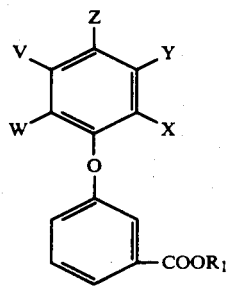 (I)

wherein
X is hydrogen, halogen, nitro, or trifluoromethyl,
Y is hydrogen or halogen,
Z is hydrogen, trifluoromethyl or nitro,
V is hydrogen, halogen, or nitro,
W is hydrogen, nitro or trifluoromethyl,
$R_1$ is hydrogen, alkyl having 1-4 carbon atoms, alkali metal, ammonium, or ammonium ion having the formula $$NH_3^+R_2 \quad (II)$$

wherein
$R_2$ is alkyl having 1-4 carbon atoms, hydroxyalkyl having 1-4 carbon atoms, alkenyl having 2-4 carbon atoms, or alkinyl having 2-4 carbon atoms,
provided that
(a) one of X, Y, Z, V and W is trifluoromethyl, and
(b) when X, Y, Z, V and W is other than hydrogen or trifluoromethyl, then no more than two substituents can be the same.

5. Method according to claim 4, which comprises using a composition containing 3-{[5-chloro-4-(trifluoromethyl)-2-nitro]-phenoxy}-benzoic acid or its salt as active ingredient.

6. Method according to claim 4, which comprises using a composition containing the sodium ammonium-, isopropyl-ammonium-, allyl-ammonium-, ethanol-ammonium- or diethyl-2-propinyl-ammonium salt of 3-{[5-chloro-4-(trifluoromethyl)-2-nitro]-phenoxy}-benzoic acid as an active ingredient.

7. Method according to claim 4, which comprises using a composition containing 3-[2-(trifluoromethyl)-phenoxy]-benzoic acid or its salt as an active ingredient.

8. Method according to claim 4, which comprises using a composition containing 3-{[2-chloro-4-(trifluoromethyl)-6-nitro]-phenoxy}-benzoic acid or its salt as an active ingredient.

9. Method according to claim 4, which comprises using a composition containing 3-{[3-chloro-4-(trifluoromethyl)]-phenoxy}-benzoic acid or its salt, as an active ingredient.

10. Method according to claim 4, which comprises using a composition containing 3-{[3-chloro-4-(trifluoromethyl)-2,6-dinitro]-phenoxy}-benzoic acid ethyl ester as an active ingredient.

11. Method according to claim 4, which comprises using a composition containing 3-{[2-chloro-4-(trifluoromethyl)-5-nitro]-phenoxy}-benzoic acid ethyl ester as an active ingredient.

12. Method according to claim 4, which comprises using a composition containing 3-{[4-(trifluoromethyl)-2,6-dinitro]-phenoxy}-benzoic acid ethyl ester as an active ingredient.

13. Method according to claim 4, which comprises using a composition containing 3-{[2-(trifluoromethyl)-

4-nitro]-phenoxy}-benzoic acid ethyl ester as an active ingredient.

14. Method according to claim 4, which comprises using a composition containing 3-{[2-chloro-4-(trifluoromethyl)-6-nitro]-phenoxy}-benzoic acid ethyl ester as an active ingredient.

15. The method of claim 4, wherein X is hydrogen chlorine, nitro, or trifluoromethyl, Y is hydrogen, or chlorine, V is hydrogen, chlorine, or nitro, R1 is ethyl, sodium, potassium R2 is isopropyl, 2-hydroxyethyl, propinyl or propargyl.

* * * * *